(12) United States Patent
Liu

(10) Patent No.: US 10,307,126 B2
(45) Date of Patent: Jun. 4, 2019

(54) COMPUTED TOMOGRAPHY PERFUSION IMAGING

(71) Applicant: SHENYANG NEUSOFT MEDICAL SYSTEMS CO., LTD., Shenyang (CN)

(72) Inventor: Yao Liu, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 749 days.

(21) Appl. No.: 14/852,386

(22) Filed: Sep. 11, 2015

(65) Prior Publication Data

US 2016/0073992 A1 Mar. 17, 2016

(30) Foreign Application Priority Data

Sep. 11, 2014 (CN) .......................... 2014 1 0462793

(51) Int. Cl.
*A61B 6/00* (2006.01)
*A61B 6/03* (2006.01)
*A61B 5/026* (2006.01)
*G01R 33/563* (2006.01)

(52) U.S. Cl.
CPC .............. *A61B 6/507* (2013.01); *A61B 6/032* (2013.01); *A61B 6/461* (2013.01); *A61B 6/486* (2013.01); *A61B 6/5217* (2013.01); *A61B 6/5247* (2013.01); *A61B 5/0263* (2013.01); *G01R 33/56366* (2013.01)

(58) Field of Classification Search
CPC ....... A61B 5/0263; A61B 6/032; A61B 6/461; A61B 6/486; A61B 6/507; A61B 6/5217; A61B 6/5247; G01R 33/56366
See application file for complete search history.

(56) References Cited

U.S. PATENT DOCUMENTS

| | | |
|---|---|---|
| 2004/0109536 A1 | 6/2004 | Shefer et al. |
| 2006/0178836 A1 | 8/2006 | Bai et al. |
| 2014/0114618 A1 | 4/2014 | Fonte et al. |
| 2014/0140474 A1 | 5/2014 | Caruso et al. |

FOREIGN PATENT DOCUMENTS

| | | |
|---|---|---|
| CN | 1048780 A | 1/1991 |
| CN | 1805712 A | 7/2006 |
| CN | 102361592 A | 2/2012 |
| CN | 102612248 A | 7/2012 |
| CN | 103186895 A | 7/2013 |
| CN | 103976750 A | 8/2014 |
| JP | 2005305024 A | 11/2005 |
| JP | 2008-499 A | 1/2008 |
| JP | 2009039330 A | 2/2009 |
| JP | 2011-238446 A | 11/2011 |
| JP | 2013027467 A | 2/2013 |

*Primary Examiner* — Ruth S Smith
(74) *Attorney, Agent, or Firm* — McCoy Russell LLP

(57) ABSTRACT

A method of computed tomography (CT) perfusion imaging includes: obtaining perfusion data by using a CT device to scan a present perfusion subject; performing calculations of the perfusion data by using two perfusion calculation methods to obtain perfusion parameters of each of said two perfusion calculation methods as initial perfusion parameters of each of said two perfusion calculation methods; performing calculations by using the initial perfusion parameters based on weights of said two perfusion calculation methods to obtain target perfusion parameters; and forming a target perfusion image of the present perfusion subject according to the target perfusion parameters.

12 Claims, 7 Drawing Sheets

COMPUTED TOMOGRAPHY PERFUSION IMAGING

CROSS-REFERENCE TO RELATED APPLICATIONS

The present application claims priority to Chinese Patent Application No. 201410462793.9, filed on Sep. 11, 2014, the entire contents of which are hereby incorporated by reference for all purposes.

BACKGROUND

In computed tomography (CT) perfusion imaging, contrast media may be injected from the vein of a subject (e.g., a patient) to specific tissues/organs, such as the brain or liver, and so on. A dynamic scan may be performed on a selected layer to obtain time density curve (TDC) of each pixel of the selected layer, perfusion parameters calculated based on the TDC using perfusion calculation methods, and then a perfusion image is formed according to calculated perfusion parameters. The perfusion image may provide microcirculation state of tissues and/or organs in which the microcirculation state is called perfusion status. For example, in the perfusion image of the brain, the gray level of each pixel of the perfusion image may represent the size of blood volume of a corresponding position in the brain. Therefore, CT perfusion imaging may reveal pathological and physiological changes, such as cerebral infarction, cancer or other diseases at a cellular level that would help in designing a treatment plan before and after surgery. The present disclosure is directed to a device and methods related to CT perfusion imaging including determining target perfusion parameters to perform a targeted perfusion image based on weights of two perfusion calculation methods.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS products are exported to over 60 countries and regions around the globe, serving more than 5,000 renowned customers. NMS' latest successful developments, such as 128 Multi-Slice CT Scanner, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject (i.e., the patient) during a CT scanning process.

BRIEF DESCRIPTION OF DRAWINGS

Features of the present disclosure are illustrated by way of example and not limited in the following figures, in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
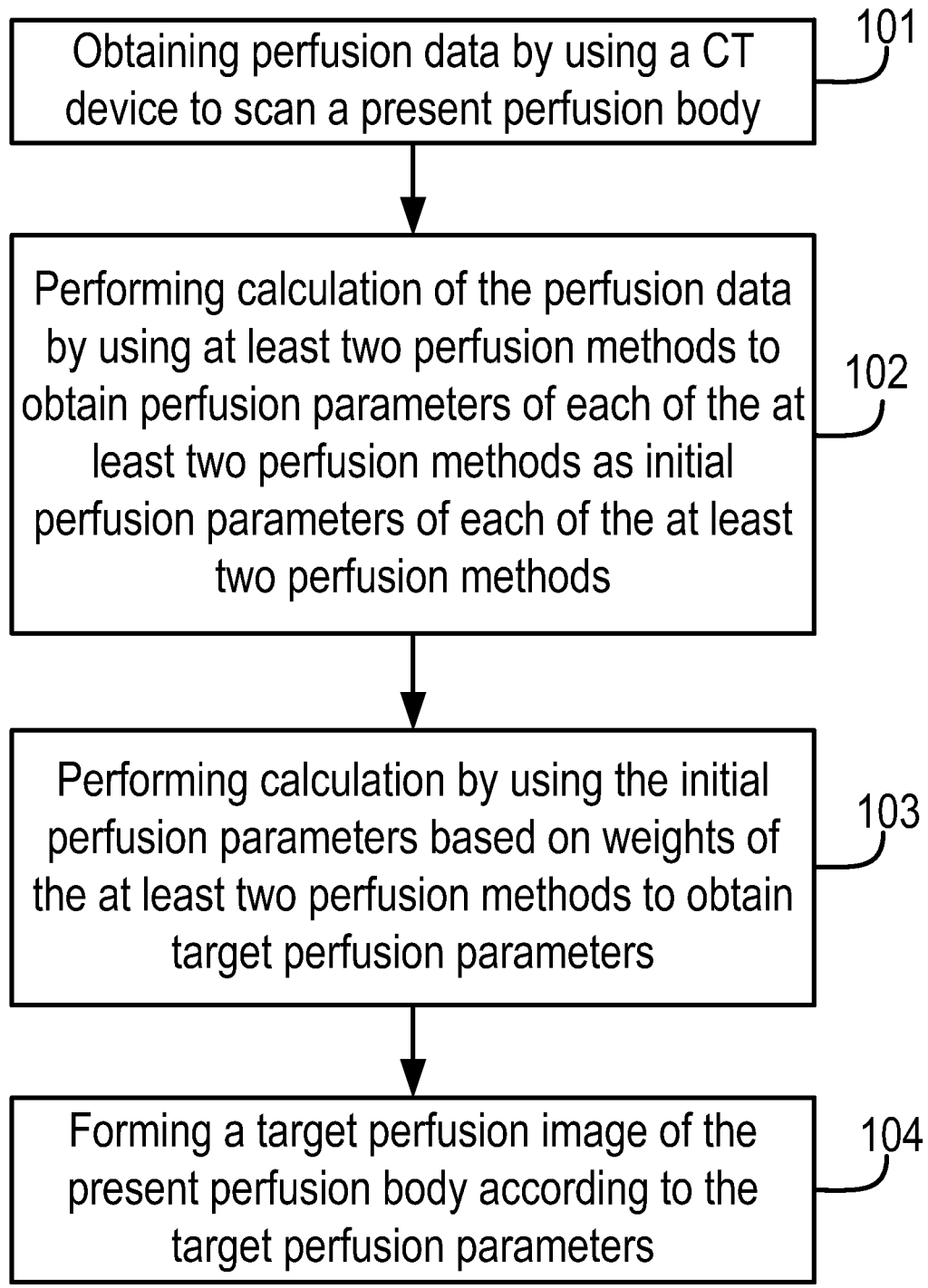
FIG. 1 is an example of a flowchart of a method of computed tomography (CT) perfusion imaging according to the present disclosure.

FIG. 1 is an example of a flowchart of a method of computed tomography (CT) perfusion imaging according to the present disclosure.

In block 101, perfusion data may be obtained using a CT device to scan a present perfusion subject. The present perfusion subject may be a patient.

In block 102, calculations of the perfusion data may be performed using each of two perfusion calculation methods, so as to obtain perfusion parameters from each of said two perfusion calculation methods as initial perfusion parameters of each of said two perfusion calculation methods.

In block 103, calculations may be performed using the initial perfusion parameters based on weights of said two perfusion calculation methods to obtain target perfusion parameters.

In block 104, a target perfusion image of the present perfusion subject may be formed according to the target perfusion parameters.

In an example, in block 101, a CT device may be used to perform a plain CT scan of the present perfusion subject, such as the subject's brain, liver, etc., to determine whether the present perfusion subject may perform the perfusion scan. After it is determined that the present perfusion subject may perform the perfusion scan, the operator may combine body weight, health degree, lesion location and type, and other information of the present perfusion subject to determine the parameters of a contrast media, wherein parameters of the contrast media may be dose or injection rate of the contrast media. Then, scan parameters, such as scan start time, length of scan time, and interval time of each image layer may be set. Finally, the CT device may automatically match a best perfusion calculation method according to the aforementioned parameters, or the operator may manually select a best perfusion calculation method. However, in another example, the relevant information of the present perfusion subject may be entered into the CT device, and then the CT device may suggest the parameters of the contrast media, set the scan parameters, and determine the best perfusion calculation method. It should be understood that the selection of the best perfusion calculation method may affect weight of a perfusion calculation method in calculations of target perfusion parameters.

After injecting the contrast media into the present perfusion subject, the CT device may perform a dynamic scan of the present perfusion subject in a selection layer to obtain perfusion data. In an example, the perfusion data may be a time density curve of each pixel in the selection layer. That is, according to the perfusion data, the time density curve may be drawn for every pixel in the selection layer.

The selection layer may be a single layer structure. In another example, the selection layer may be a multi-layer structure. The selection layer may be determined according to distribution of the contrast media. For example, for the CT perfusion image of the brain, a basal ganglia layer may be selected as the selection layer. It may be able to more fully include the thalamus, basal ganglia, internal capsule, anterior cerebral artery, middle cerebral artery, posterior cerebral artery, and so on. For the case of the selection layer being the multi-layer structure, a main artery, which blood flows into the tissues and organs of the perfusion subject may be selected in a first layer, and a main vein, which blood flows out the tissues and organs of the perfusion subject may be selected in a second layer. The perfusion parameters of lesion areas may be calculated based on the selected main artery, the selected main vein and a lesion area. It should be understood that that the arteries, the veins, and the lesion area may be in the same layer or may be in different layers. The selection of vessel and lesion area may be automatically determined by the CT scanner system, or the selection of vessel and lesion area may be manually adjusted by the operator in a situation that the determination of the CT scanner system is not accurate. In case of the selection layer being a multi-layer structure, it may form a three-dimensional perfusion image to provide the lesion volume and other information to the operator.

The perfusion parameters which are used to form the perfusion image may be one or more of blood volume (BV), blood flow (BF), mean transit time (MTT), transit time to peak (TTP), permeability surface (PS) and other parameters. It should be understood that perfusion parameters may be selected according to the tissues and organs of the perfusion subject. For example, in a brain perfusion, the brain's blood volume, brain's blood flow, brain's mean transit time, brain's peak time and other parameters may be selected as the perfusion parameters. For liver perfusion, the liver's blood volume, liver's blood flow, liver's mean transit time, liver's permeability surface and other parameters may be selected as the perfusion parameters. For other tissue and organ perfusion, the blood volume, the blood flow, the mean transit time, the permeability surface and other parameters of the said tissue or organ may be selected as the perfusion parameters.

In an example of block 102, calculations of the perfusion data may be performed using two perfusion calculation methods. That is two or more existing perfusion calculation methods may be used to calculate the perfusion data, in which existing perfusion calculation methods include the moments method, the maximum slope method, the de-convolution method, the patlak analysis method, etc. It should be understood that the perfusion calculation methods may be selected according to the tissues and organs of the perfusion subject. For example, in brain perfusion, it may select the maximum slope method and the de-convolution method as the two perfusion calculation methods. For liver perfusion, it may select the de-convolution method of dual-input one-compartmental mode and the maximum slope method as the perfusion calculation methods, in which the maximum slope method may use the spleen strengthen peak time as the demarcation point of the hepatic artery and portal vein. For other tissue and organ perfusion, it may select the maximum slope method, the de-convolution method, and the patlak analysis method as the perfusion calculation methods.

Different perfusion calculation methods are usually based on different assumptions. There may be deviations between the initial perfusion parameters which are calculated by using different perfusion calculation methods and the real perfusion parameters.

The moments method was proposed by Axel in 1980. Its theoretical foundation is the diluted contrast agent theory. That is, in the assumption of the absence of extravasation of contrast agents and the elimination recirculation of contrast agents, it may calculate the bleeding capacity based on the time density curve. The principle advantage of the moments method is that it simplifies calculations of perfusion. A ratio of the blood volume and the mean transit time may be used as the blood flow without the assumption of no venous drainage. In general, the assumption of a ratio being constant is not realistic, especially in ischemic tissues, in which the ratio is a variance of transit time of the organ divided by the mean transit time.

The maximum slope method was proposed by Peters in 1987. Peters believed that when the scanning time length is less than the minimum time of a contrast agent transiting an organ, all injected contrast agents may remain in the vessel of the tissue of the organ without an outflow from the vein. That is, it may be assumed that there is no contrast agents outflow from the vein during the minimum transit time from the contrast agents being injected into the artery. The blood flow of the tissues and organs may equal the ratio of the maximum initial slope of the TDC of the organ of the perfusion subject and the magnitude of the peak value of the artery TDC. The advantage of the maximum slope method is that the concept is simple and easy to understand. The assumption of no contrast agents outflowing from the vein at the maximum initial slope of the TDC is difficult to achieve. If there is significant venous outflow at the maximum initial slope of the TDC, the blood flow may be underestimated. In addition, it may increase the injection rate and dose of contrast agent, for example, using intravenous cannula to increase the injection rate up to 10 ml/s-20 ml/s, to shorten the time to reach the maximum initial slope for ensuring the accuracy of calculations of the maximum slope method. However, this injection is not suitable for patients with adverse cardiac function or fragile veins, so the maximum slope method is limited in clinical application.

A multi-temporal graphical analysis method may be used to perform transformations for TDCs of the interest tissue region and the artery which is injected with the contrast agent, and perform a linear fitting of a data curve in certain conditions. Thus, in different graphical analysis method, the slope of a line generated by the linear fitting may represent absorption rate or distribution volume of the contrast agent. The advantage of the multi-temporal graphical analysis method is that it may be independent of any particular model structure. In general, the fitting method in the multi-temporal graphical analysis method may provide a better fit based on the observations in tumor tissue. That is, the diversity of observations may be small and the observations may be more stable. The disadvantage of the multi-temporal graphical analysis method is the assumption that the contrast agent cannot reflux from the tissue. This assumption may only occur at the initial time in which the contraction of the contrast agent has a dramatic change and in the tissue compartment model in which the concentration curve of the contrast agent declines slowly enough. Moreover, the long-time graphical analysis method may also ignore the vascular volume.

The de-convolution method was proposed by Cenic in 1900. It assumes that the research system is in an ideal state and is a linear time-invariant system. It may obtain the impulse response function (IRF) of the tissue according to the tissue enhancement curve which is generated using the instantaneous injection of unit mass of contrast agent. It may reflect the distribution of the contrast agent in the tissue in time domain. The advantage of the de-convolution method is that the injection rate of the contrast agent can be quite low, generally the injection rate can be 3.5 ml/s to 4.0 ml/s. The de-convolution method is widely used in clinical application. However, the disadvantage of the de-convolution method is the assumption that the contrast agent is non-proliferating, which is a reasonable assumption for cerebral perfusion. But this assumption is neither appropriate for other organ perfusion, nor appropriate for the blood-brain barrier (BBB) of a brain tumor. In addition, the de-convolution method is particularly sensitive to noise. Noise must be suppressed by an effective method to ensure the accuracy of calculations of the de-convolution method.

In addition, the perfusion calculation method with delay-sensitive may assume there is no perfusion in the tissue before the start of perfusion of the artery. In comparison with the delay-insensitive perfusion calculation method, the perfusion calculation method with delay-sensitive may enlarge the estimation of an area of artery stroke. For example, it may enlarge the estimation of the area of brain stroke.

In block 103, the weights of said two perfusion calculation methods are obtained from machine learning of corresponding relationships between perfusion parameters of each of said two perfusion calculation methods for a history perfusion subject and real perfusion parameters of the history perfusion subject. The machine learning may be any machine learning method that implements machine learning function. For example, the machine learning method may be artificial neural networks, a support vector machine, Ada-Boost algorithm, and Bayesian networks, etc.

In an example, some history perfusion subjects with known real perfusion parameters may be obtained. The history perfusion parameters of the history perfusion subjects may be calculated using the aforementioned perfusion calculation methods. The machine learning of corresponding relationships between the history perfusion parameters and the real perfusion parameters of the history perfusion subjects may be performed, wherein the history perfusion parameters were previous calculations of the history perfusion subjects by the aforementioned perfusion calculation methods. Then, a machine learning model may be established, which may represent the relationships between the calculated perfusion parameters and the real perfusion parameters, in which the calculated perfusion parameters are calculated of the perfusion subjects by the aforementioned perfusion calculation methods. Finally, the weights of the corresponding perfusion calculation methods may be determined according to the machine learning model. The history perfusion parameters of the history perfusion subjects may be obtained by using the aforementioned perfusion calculation methods to preform CT perfusion imaging of the history perfusion subjects. The real perfusion parameters of the history perfusion subjects may be obtained by an anatomical analysis of the history perfusion subjects. In another example of the present disclosure, the perfusion image of the perfusion subject obtained by using magnetic resonance imaging (MRI) may be very close to the real perfusion status. For example, the real perfusion parameters of the history perfusion subjects may be obtained by using the MRI to perform perfusion imaging of the history perfusion subjects. Thus, enough training data for machine learning may be obtained.

When perfusion imaging is performed on a present perfusion subject with unknown true perfusion parameters, the weights of the corresponding perfusion calculation methods according to the established machine learning model may be obtained. Weighting calculations of the initial perfusion parameters of the present perfusion subject may be performed to obtain the target perfusion parameters, in which the weighting calculations may be a weighting addition. Thus, in comparison with the initial perfusion parameters, the target perfusion parameters may be more close to the real perfusion parameters of the present perfusion subject. According to an example of the present disclosure, the established machine learning model may be calculation tools that may represent the relationships between the variable values of multi-input variables and the variable values of multi-output variables. The multi-input variables may be the perfusion parameters of the perfusion subjects which may be calculated by the aforementioned perfusion calculation methods, and the multi-output variables may be the real perfusion parameters. That is, the initial perfusion parameters may be used as the multi-input variables, and the machine learning model may be used to calculate the real perfusion parameters of the present perfusion subject, in which the real perfusion parameters are the multi-output variables, which may ensure that the calculated target perfusion parameters are close to the real perfusion parameters of the present perfusion subject.

In addition, for different tissues and organs, the same machine learning model or separately set up different machine learning models may be established. In the examples of the present disclosure, it may determine which tissues and organs can use the same machine learning model based on the characteristics of the blood supply of the tissues and organs. For example, for kidney and pancreas, both of which are organs with a single artery system, the blood flow characteristics are relatively close, so kidney and pancreas may share the same machine learning model. Similarly, for different diseases, the same machine learning model may be used, or different machine learning models may be created to use.

In block 104, according to an example of the present disclosure, when the target perfusion image of the present perfusion subject is formed based on the target perfusion parameters, the target perfusion parameters of each pixel of the selection layer may be used to determine gray level or color level of the corresponding pixel in the target perfusion image for generating the target perfusion image.

Figure 2:
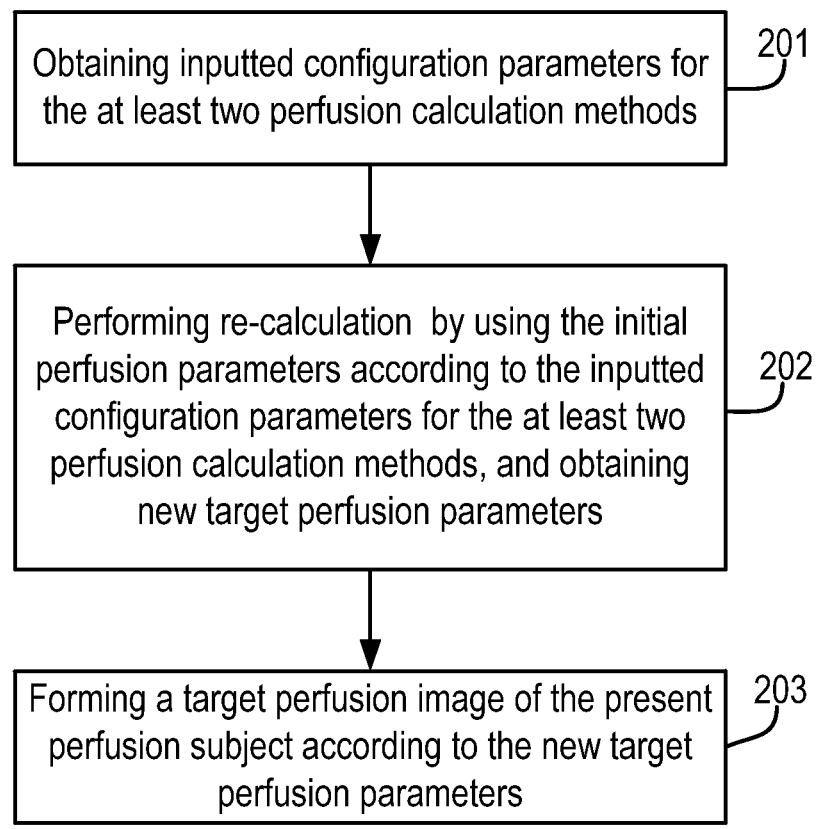
FIG. 2 is an example of a flowchart of a method for modifying weights of perfusion calculation methods according to the present disclosure.

In addition, the generated target perfusion image may be displayed in response to a display request of the operator. Thus, the operator may review the perfusion status of the present perfusion subject in the target perfusion image. In examples of the present disclosure, the operator may enter the configuration coefficients of the corresponding perfusion calculation method to adjust the target perfusion images. Therefore, the target perfusion images obtained may reflect the real perfusion status more accurately. FIG. 2 is an example of a flowchart of a method for modifying weights of perfusion calculation methods according to the present disclosure.

In block 201, inputted configuration coefficients for the two perfusion calculation methods may be obtained.

In block 202, according to the inputted configuration coefficients for said two perfusion calculation methods, re-calculations may be performed using initial perfusion parameters of said perfusion calculation methods to obtain new target perfusion parameters.

In block 203, a target perfusion image of the present perfusion subject may be performed according to the new target perfusion parameters.

In an example, in displaying the target perfusion image to the operator, an operation method for inputting configuration coefficients may be simultaneously provided to adjust the target perfusion image. When the operator performs the modification operation of the weights, the inputted configuration coefficients for said two perfusion calculation methods in response to the modification operation may be obtained to regenerate the target perfusion image.

Then, configuration coefficients may be used as the ratio of the initial perfusion parameters of said two perfusion calculation methods in the target perfusion parameters, wherein the configuration coefficients are inputted by the operator for said two perfusion calculation methods. Multiplications may be summed as the target perfusion parameter, in which each multiplication is the product of the initial perfusion parameter and the corresponding configuration coefficient.

After re-generating the target perfusion image, a re-generated target perfusion image is displayed to the operator. It may be understood that if image quality of the re-generated target perfusion image is still not good enough, the operator may re-input the configuration coefficients for said two perfusion calculation methods and re-generate the target perfusion image again. The aforementioned operations may be iteratively performed until the image quality of the target perfusion image is good.

In addition, according to some examples of the present disclosure, a group of the configuration coefficients for said two perfusion calculation methods may be saved. A saved group of configuration coefficients may be used by another operator for reference so as to simplify the operation of the other operator. It may also use the initial perfusion parameters and the target perfusion parameters as a group of training data for re-training the machine learning model, in which the target perfusion parameters are obtained according to the initial perfusion parameters and the configuration coefficients.

In order to help the operator to more easily locate the lesion area, areas in the target perfusion image that have been pathologically changed may be determined according to the target perfusion parameters of the pixels of the target perfusion image, and lesion areas are displayed. For example, in examples of the present disclosure, the CT perfusion imaging method may further include the following operations: According to the perfusion parameters of the pixels of the target perfusion image, pixels of the target perfusion image may be searched with the target perfusion parameters being in a predetermined range. An area corresponding to the searched pixels of the target perfusion image may be assigned to the lesion area, and information of the lesion area may be provided. For identifying lesion areas of different diseases, different target perfusion parameters may be selected, or different predetermined ranges may be selected for the same target perfusion parameter. The lesion information may be the lesion, grade malignancy, area of lesion, and so on.

It may be understood that an operator may compare and analyze the initial perfusion images and the target perfusion image, in which the initial perfusion images are generated by the initial perfusion parameters under each of said two perfusion calculation methods and the target perfusion image is generated by combining said two perfusion calculation methods. In order to facilitate the comparison and analysis, in an example of the present disclosure, the CT perfusion imaging method may further include the following operations: The perfusion images of the present perfusion subject may be formed corresponding to the initial perfusion parameters of each of said two perfusion calculation methods. The perfusion images may be assigned to initial perfusion images, and the initial perfusion images and the target perfusion image may be displayed. The initial perfusion images and the target perfusion image may be simultaneously displayed. For example, it may simultaneously display the initial perfusion images and the target perfusion image on a display screen. According to another example of the present disclosure, after forming the initial perfusion images and the target perfusion image, the operator may be provided with an option to select an operation mode or which perfusion images to display on the display screen. In response to the selection of the operator, the perfusion images which are selected from the initial perfusion images and the target perfusion image by the operator may be displayed.

In addition, the operator may compare and analyze the initial perfusion parameters and the target perfusion parameters at the same region in the perfusion image, in which the initial perfusion parameters may correspond to each of said two perfusion calculation methods and the target perfusion parameters are the combination of said two perfusion calculation methods. In order to facilitate the comparison and analysis, in an example of the present disclosure, the CT perfusion imaging method may further include the following operations. The initial perfusion parameters and the target perfusion parameter in a perfusion image may be simultaneously displayed. In the example of simultaneously displaying the initial perfusion parameters and the target perfusion parameter in the target perfusion image, the CT perfusion imaging method may further include the following operations. In response to a request operation of displaying the perfusion parameters of a select position in the target perfusion image, the target perfusion parameters and the initial perfusion parameters may be searched according to a select region, and the target perfusion parameters and the initial perfusion parameters corresponding to the select region may be displayed. In simultaneous display of the initial perfusion parameters and the target perfusion parameters, the initial perfusion parameters and the target perfusion parameters of the select region may be put into a table and display the table, which may facilitate the operator to compare the perfusion parameters. It may be understood that the aforementioned example is a simultaneous display of the perfusion parameters in the target perfusion image. With a combination of the previous descriptions, the perfusion parameters in a specific initial perfusion image or some initial perfusion images may be simultaneously displayed.

According to the present disclosure, the perfusion image may be generated according to the target perfusion parameters and the target perfusion parameters are obtained according to the combination of initial perfusion parameters corresponding to said two perfusion calculation methods. Thus, each of the perfusion calculation methods may compensate for the unrealistic assumptions of the other, so that the target perfusion parameters may be closer to the real perfusion parameters. It may not only make the perfusion images more accurate, but also avoid frequent operation owing to the quality of the perfusion images not being good enough.

Figure 3:
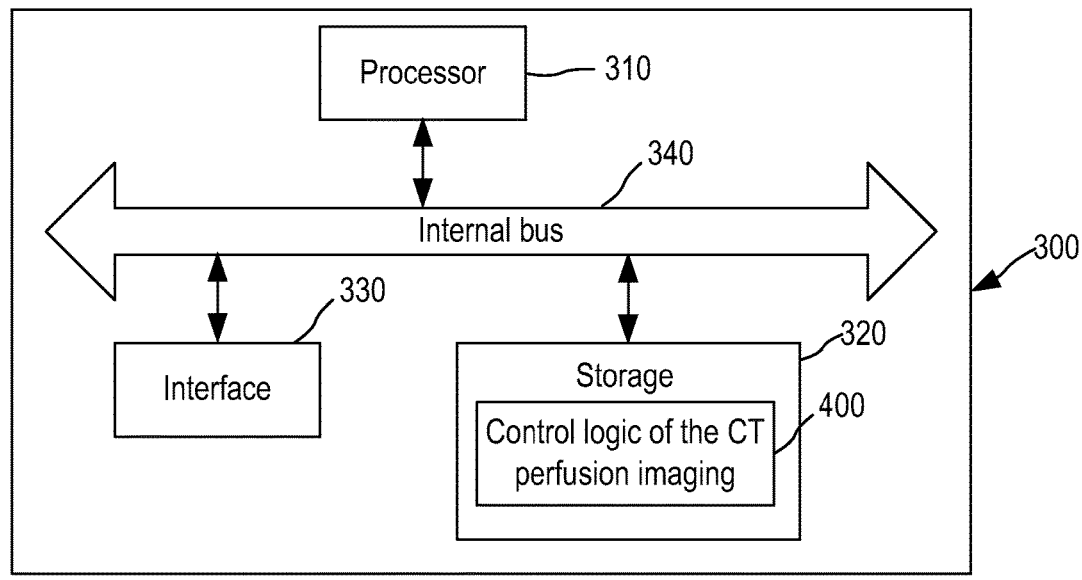
FIG. 3 is a schematic diagram of a hardware structure of a CT perfusion imaging device according to an example of the present disclosure.

FIG. 3 is a schematic diagram of a hardware structure of a CT perfusion imaging device according to an example of the present disclosure. As shown in FIG. 3, the CT perfusion imaging device 300 may include a processor 310 (e.g., a central processing unit, CPU) and a storage 320. The storage 320 is accessible by the processor 310 through an internal bus 340. In a possible example, a device 300 may further include an external interface 330 for communicating with another device or other modules. The storage 320 stores a control logic of the CT perfusion imaging 400 of machine readable instructions executable by the processor 310.

The storage 320 in which the machine readable instructions are stored may be a non-volatile memory or storage media including by way of example semiconductor memory devices, (e.g., EPROM, EEPROM, DRAM and flash memory devices; magnetic disks, e.g., internal hard disks or removable disks; magneto optical disks; and CD ROM and DVD-ROM disks). The processor 310 of the CT perfusion imaging device 300 reads the instructions of the corresponding modules of the control logic of the CT perfusion imaging 400 stored in the storage 320 and executes the instructions.

Figure 4:
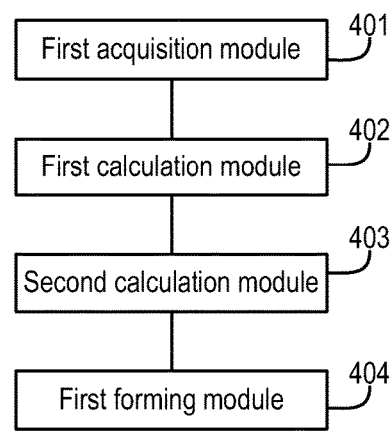
FIG. 4 is a schematic diagram of function modules of control logic of a CT perfusion imaging according to an example of the present disclosure.

FIG. 4 is a schematic diagram of function modules of the control logic of the CT perfusion imaging 400 according to an example of the present disclosure. As shown in FIG. 4, the function modules of the control logic of the CT perfusion imaging 400 may be corresponding to the method shown in FIG. 1. The control logic of the CT perfusion imaging 400 may include a first acquisition module 401, a first calculation module 402, a second calculation module 403 and a first forming module 404.

The first acquisition module 401 may be used to obtain perfusion data by using the CT device to scan a present perfusion subject The first calculation module 402 may be used to perform calculations of the perfusion data by using each of two perfusion calculation methods, obtain the perfusion parameters of said two perfusion calculation methods, and assign the obtained perfusion parameters to the initial perfusion parameters.

The second calculation module 403 may be used to perform calculations by using the initial perfusion parameters based on weights of said two perfusion calculation methods to obtain the target perfusion parameters.

The first forming module 404 may be used to form a target perfusion image of the present perfusion subject according to the target perfusion parameters.

According to examples of the present disclosure, the weights of said two perfusion calculation methods are obtained from the machine learning of corresponding relationships between the perfusion parameters and the real perfusion parameters of a history perfusion subject, wherein the perfusion parameters were previous calculations of history perfusion subject by said two perfusion calculation methods.

According to examples of the present disclosure, the real perfusion parameters of the history perfusion subjects may be obtained using magnetic resonance imaging (MRI) to perform perfusion imaging of the history perfusion subject.

Figure 5:
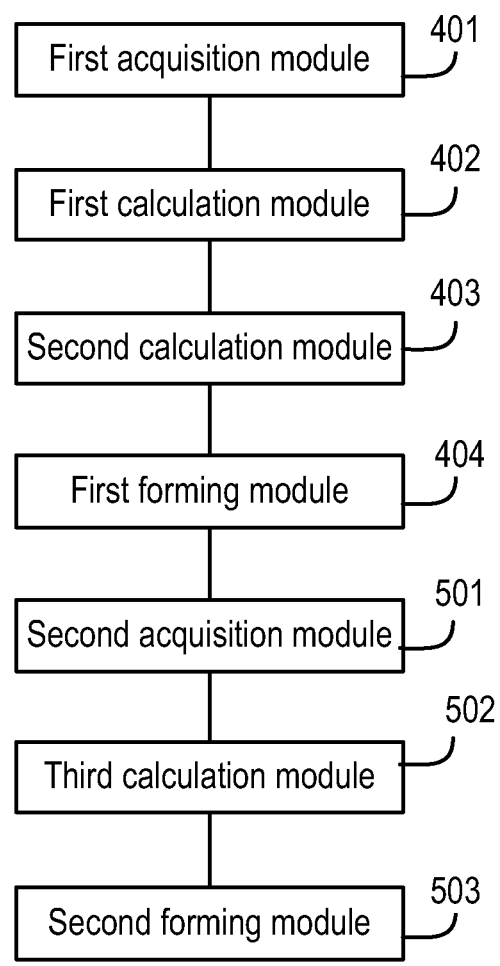
FIG. 5 is another schematic diagram of function modules of control logic of a CT perfusion imaging according to an example of the present disclosure.

FIG. 5 is another schematic diagram of function modules of the control logic of the CT perfusion imaging according to an example of the present disclosure. According to the example shown in FIG. 5, in addition to the function modules in FIG. 4, it may further include a second acquisition module 501, a third calculation module 502, and a second forming module 503.

The second acquisition module 501 may be used to obtain the inputted configuration coefficients for said two perfusion calculation methods in response to input operations of the configuration coefficients.

The third calculation module 502 may be used to perform the re-calculations by using the initial perfusion parameters according to the inputted configuration coefficients for said two perfusion calculation methods, and so as to obtain new target perfusion parameters.

Figure 6:
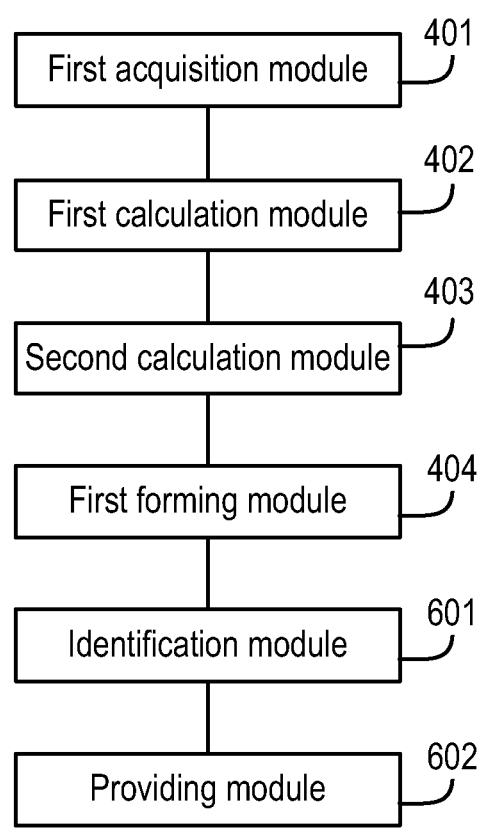
FIG. 6 is still another other schematic diagram of function modules of control logic of a CT perfusion imaging according to an example of the present disclosure.

The second forming module 503 may be used to form a target perfusion image of the present perfusion subject according to the new target perfusion parameters FIG. 6 is another schematic diagram of function modules of the control logic of the CT perfusion imaging according to an example of the present disclosure. According to the example shown in FIG. 6, in addition to the function modules in FIG. 4, it may further include an identification module 601 and a providing module 602.

The identification module 601 may be used to identify the lesion areas in the target perfusion image according to the target perfusion parameters of pixels of the target perfusion image.

The providing module 602 may be used to provide the lesion information of the lesion areas.

Figure 7:
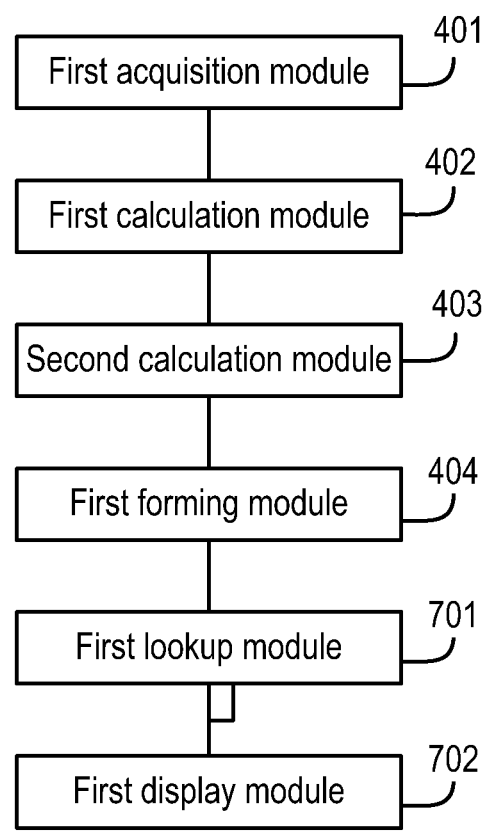
FIG. 7 is yet another schematic diagram of function modules of control logic of a CT perfusion imaging according to an example of the present disclosure.

FIG. 7 is yet another schematic diagram of function modules of the control logic of the CT perfusion imaging according to an example of the present disclosure. According to the example shown in FIG. 7, in addition to the function modules in FIG. 4, it may further include a first lookup module 701 and a first display module 702.

The first lookup module 701 may be used to search the target perfusion parameters and the initial perfusion parameters according to a select position in response to a request operation of displaying the perfusion parameters of the select position in the target perfusion image.

The first display module 702 may be used to display the target perfusion parameters and the initial perfusion parameters corresponding to the select position.

Figure 8:
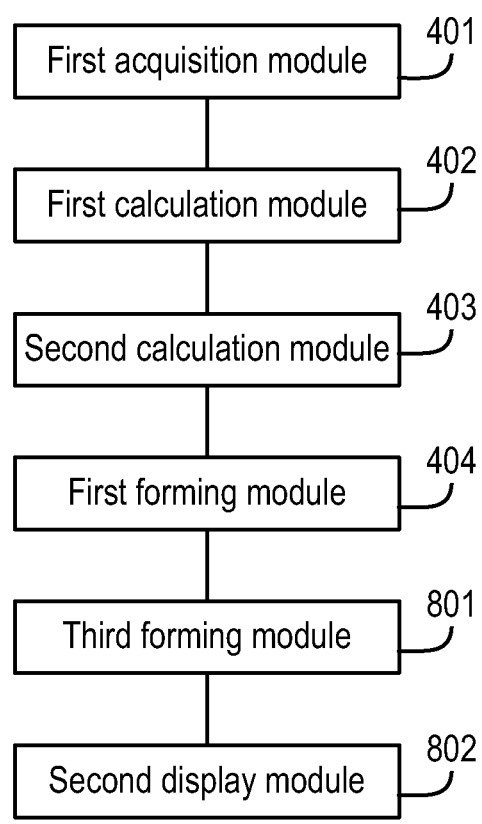
FIG. 8 is yet another schematic diagram of function modules of control logic of a CT perfusion imaging according to an example of the present disclosure.

FIG. 8 is yet another schematic diagram of function modules of the control logic of a CT perfusion imaging according to an example of the present disclosure. According to the example shown in FIG. 8, in addition to the function modules in FIG. 4, it may further include a third forming module 801 and a second display module 802.

The third forming module 801 may be used to form the perfusion images of the present perfusion subject corresponding to the initial perfusion parameters of each of said two perfusion calculation methods, and assign the perfusion images to initial perfusion images.

The second display module 802 may be used to display the initial perfusion images and the target perfusion image.

The following technology may be implemented in software which is described in the operation of the control logic of the CT perfusion imaging 400 of the CT perfusion imaging device 300: The storage 320 stores the control logic of the CT perfusion imaging 400 of machine readable instructions executable by the processor 310. The processor 310 of the CT perfusion imaging device 300 reads the instructions of the corresponding modules of the control logic of the CT perfusion imaging 400 stored in the storage 320 and executes the instructions.

The instructions executed by the processor 310 may cause the processor 310 to perform the following operations:

The processor 310 may obtain perfusion data by using a CT device to scan a present perfusion subject, wherein the perfusion data is a time density curve.

The processor 310 may perform calculations of the perfusion data by using said two perfusion calculation methods to obtain the perfusion parameters of each of said two perfusion calculation methods as the initial perfusion parameters of each of said two perfusion calculation methods.

The processor 310 may perform calculations by using the initial perfusion parameters based on the weights of said two perfusion calculation methods to obtain the target perfusion parameters.

The processor 310 may form a target perfusion image of the present perfusion subject according to the target perfusion parameters.

Further, the instructions executed by the processor 310 may cause the processor 310 to perform the following operation:

The processor 310 may obtain the inputted configuration coefficients for said two perfusion calculation methods in response to the input operations of the configuration coefficients.

The processor 310 may perform re-calculations by using the initial perfusion parameters according to the inputted configuration coefficients for said two perfusion calculation methods to obtain new target perfusion parameters.

The processor 310 may form the target perfusion image of the present perfusion subject according to the new target perfusion parameters.

Further, the instructions executed by the processor 310 may cause the processor 310 to perform the following operation:

The processor 310 may identify lesion areas in the target perfusion image according to the target perfusion parameters of pixels of the target perfusion image, and provide lesion information of the lesion areas.

Further, the instructions executed by the processor 310 may cause the processor 310 to perform the following operation:

The processor 310 may search the target perfusion parameters and the initial perfusion parameters according to the select region in response to a request operation of displaying the perfusion parameters of the select region in the target perfusion image, and display the target perfusion parameters and the initial perfusion parameters corresponding to the select region.

Further, the instructions executed by the processor 310 may cause the processor 310 to perform the following operation:

The processor 310 may form the perfusion images of the present perfusion subject as initial perfusion images by using the initial perfusion parameters of each of said two perfusion calculation methods, and display the initial perfusion images and the target perfusion image.

The above are only preferred examples of the present invention and are not intended to limit the invention. Within the spirit and principles of the present invention, any changes made, equivalent replacement, or improvement in the protection of the present invention may be contained within the range.

The methods, processes and units described herein may be implemented by hardware (including hardware logic circuitry), software or firmware, or a combination thereof.

The term "processor" is to be interpreted broadly to include a processing unit, ASIC, logic unit, or programmable gate array, etc. The processes, methods and functional units may all be performed by the one or more processors; reference in this disclosure or the claims to a "processor" should thus be interpreted to mean "one or more processors".

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of computed tomography (CT) perfusion imaging, comprising:
    obtaining perfusion data by using a CT device to scan a present perfusion subject;
    performing calculations of the perfusion data by using two perfusion calculation methods to obtain perfusion parameters of each of said two perfusion calculation methods as initial perfusion parameters of each of said two perfusion calculation methods;
    performing calculations by using the initial perfusion parameters based on weights of said two perfusion calculation methods to obtain target perfusion parameters; and
    forming a target perfusion image of the present perfusion subject according to the target perfusion parameters.

2. The method of claim 1, wherein the perfusion data is a time density curve.

3. The method according to claim 1, further comprising:
    obtaining inputted configuration coefficients for said two perfusion calculation methods in response to input operations of the configuration coefficients;
    performing re-calculations by using the initial perfusion parameters according to the inputted configuration coefficients for said two perfusion calculation methods to obtain new target perfusion parameters; and forming the target perfusion image of the present perfusion subject according to the new target perfusion parameters.

4. The method according to claim 1, further comprising:

identifying lesion areas in the target perfusion image according to the target perfusion parameters of pixels of the target perfusion image, and providing lesion information of the lesion areas.

5. The method according to claim 1, further comprising:

searching the target perfusion parameters and the initial perfusion parameters according to a select region in response to a request operation of displaying the perfusion parameters of the select region in the target perfusion image, and displaying the target perfusion parameters and the initial perfusion parameters corresponding to the select region.

6. The method according to claim 1, further comprising:

forming perfusion images of the present perfusion subject as initial perfusion images by using the initial perfusion parameters of each of said two perfusion calculation methods; and displaying the initial perfusion images and the target perfusion image.

7. A device for forming a computed tomography (CT) perfusion image, comprising:

a storage medium to store machine readable instructions of a control logic for CT perfusion imaging; and a processor which reads and executes the machine readable instructions to:

obtain perfusion data by using a CT device to scan a present perfusion subject;

perform calculations of the perfusion data by using two perfusion calculation methods to obtain perfusion parameters of each of said two perfusion calculation methods as initial perfusion parameters of each of said two perfusion calculation methods;

perform calculations by using the initial perfusion parameters based on weights of said two perfusion calculation methods to obtain target perfusion parameters; and form a target perfusion image of the present perfusion subject according to the target perfusion parameters.

8. The device according to claim 7, wherein the perfusion data is a time density curve.

9. The device according to claim 7, wherein the machine readable instructions further cause the processor to:

obtain inputted configuration coefficients for said two perfusion calculation methods in response to input operations of the configuration coefficients;

perform re-calculations by using the initial perfusion parameters according to the inputted configuration coefficients for said two perfusion calculation methods to obtain new target perfusion parameters; and form a target perfusion image of the present perfusion subject according to the new target perfusion parameters.

10. The device according to claim 7, wherein the machine readable instructions further cause the processor to:

identify lesion areas in the target perfusion image according to the target perfusion parameters of pixels of the target perfusion image, and provide lesion information of the lesion areas.

11. The device according to claim 7, wherein the machine readable instructions further cause the processor to:

search the target perfusion parameters and the initial perfusion parameters according to a select position in response to a request operation of displaying the perfusion parameters of the select region in the target perfusion image, and display the target perfusion parameters and the initial perfusion parameters corresponding to the select region.

12. The device according to claim 7, wherein the machine readable instructions further cause the processor to:

form perfusion images of the present perfusion subject as initial perfusion images by using the initial perfusion parameters of each of said two perfusion calculation methods; and display the initial perfusion images and the target perfusion image.

* * * * *